United States Patent
Park et al.

(10) Patent No.: US 11,200,985 B2
(45) Date of Patent: Dec. 14, 2021

(54) UTILIZING UNSTRUCTURED LITERATURE AND WEB DATA TO GUIDE STUDY DESIGN IN HEALTHCARE DATABASES

(71) Applicant: International Business Machines Corporation, Armonk, NY (US)

(72) Inventors: Yoonyoung Park, Cambridge, MA (US); Fang Lu, Cambridge, MA (US); Amar Das, Cambridge, MA (US); Uri Kartoun, Cambridge, MA (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 283 days.

(21) Appl. No.: 16/167,600

(22) Filed: Oct. 23, 2018

(65) Prior Publication Data

US 2020/0126675 A1  Apr. 23, 2020

(51) Int. Cl.
*G16H 50/70* (2018.01)
*G06F 16/34* (2019.01)
*G06F 16/332* (2019.01)

(52) U.S. Cl.
CPC ......... *G16H 50/70* (2018.01); *G06F 16/3329* (2019.01); *G06F 16/345* (2019.01)

(58) Field of Classification Search
CPC ........ G16H 50/00; G16H 50/20; G16H 50/30; G16H 50/50; G16H 50/70; G16H 50/80; G06F 16/3326; G06F 16/3328; G06F 16/3329; G06F 16/338; G06F 16/34; G06F 16/345; G06F 19/30; G06F 19/32; G06F 19/34; G06Q 50/22; G06Q 50/24
USPC ....................................................... 705/2, 3
See application file for complete search history.

(56) References Cited

U.S. PATENT DOCUMENTS

| 2014/0108380 A1* | 4/2014 | Gotz ................. G06F 16/904 707/722 |
| 2014/0181125 A1* | 6/2014 | Moitra ............... G06F 16/951 707/749 |
| 2014/0350961 A1 | 11/2014 | Csurka et al. |
| 2015/0324527 A1 | 11/2015 | Siegel et al. |

(Continued)

FOREIGN PATENT DOCUMENTS

EP    2973059    1/2016

OTHER PUBLICATIONS

Swapna Abhyankar, Dina Demner-Fushman, Fiona M Callaghan, Clement J McDonald, Combining structured and unstructured data to identify a cohort of ICU patients who received dialysis, Journal of the American Medical Informatics Association, vol. 21, Issue 5, Sep. 2014, pp. 801-807 (Year: 2014).*

(Continued)

*Primary Examiner* — Hiep V Nguyen
*Assistant Examiner* — Christopher B Wehrly
(74) *Attorney, Agent, or Firm* — Peter Edwards, Esq.; McGinn I.P. Law Group, PLLC.

(57) ABSTRACT

A study design guide method, system, and computer program product, include specifying a search parameter, analyzing a collection of unstructured documents using the search parameter, creating a list of informative terms and informative phrases related to design of a study cohort, and creating a visualization reflecting a level of importance, a frequency, and a relevancy of the informative terms and the informative phrases in relation to each other for a study design using the study cohort.

13 Claims, 8 Drawing Sheets

(56) References Cited

U.S. PATENT DOCUMENTS

| | | | |
|---|---|---|---|
| 2016/0196394 A1* | 7/2016 | Chanthasiriphan | ........................... G06Q 10/0635 705/2 |
| 2016/0283069 A1* | 9/2016 | Gupta | .................... G06Q 10/10 |
| 2018/0300640 A1* | 10/2018 | Birnbaum | .............. G16H 10/20 |
| 2019/0295727 A1* | 9/2019 | Xanthakis | ............ A61B 5/7275 |

OTHER PUBLICATIONS

Mel et al. "The NIST Definition of Cloud Computing", Recommendations of the National Institute of Standards and Technology, Nov. 16, 2015.

Elizabeth S. Chen et al.; "Automated Acquisition of Disease-Drug Knowledge from Biomedical and Clinical Documents: An Initial Study"; NCBI; Journal of the American Medical Informatics Association, vol. 15, No. 1, Jan./Feb. 2008.p.

* cited by examiner

UTILIZING UNSTRUCTURED LITERATURE AND WEB DATA TO GUIDE STUDY DESIGN IN HEALTHCARE DATABASES

BACKGROUND

The present invention relates generally to a study design guide method, and more particularly, but not by way of limitation, to a system, method, and recording medium for quickly analyzing a large amount of unstructured data and obtaining insights for cohort selection criteria and study design.

Clinical or other studies using observational databases (e.g. electronic medical records (EMR), claims data, social media/news data, etc.) require a defined study cohort. Conventionally; the very first step of research is to determine the cohort, which in turn may determine the overall validity. Cohort defining process is iterative and requires human experts' knowledge in the study field as well as in the database.

The burden of justifying study design and cohort criteria is on the researcher. Previous literature is used as standards for defining the cohort criteria. However, using the literature is time consuming and it is easy to miss important prior publications (e.g., human error). It also is possible to have a cohort that cannot be mapped to a definable subpopulation that lacks generalizability And, if the quality of the variables used to implement selection criteria is poor or the actual meanings of the variables are different from the users' expectation, then validity of the cohort will be questionable which is often the case in secondary healthcare database-like claims or EMR.

Conventional techniques include largely data query tools that do not provide any support for shaping the study rationale, where input from a human expert is most needed. Thus, there is a need in the art for a data exploration tool to more efficiently interrogate large databases.

SUMMARY

In an exemplary embodiment, the present invention can provide a computer-implemented study design guide method, the method including specifying a search parameter, analyzing a collection of unstructured documents using the search parameter, creating a list of informative terms and informative phrases related to design of a study cohort, and creating a visualization reflecting a level of importance, a frequency, and a relevancy of the informative terms and the informative phrases in relation to each other for a study design using the study cohort. One or more other exemplary embodiments include a computer program product and a system.

Other details and embodiments of the invention will be described below, so that the present contribution to the art can be better appreciated. Nonetheless, the invention is not limited in its application to such details, phraseology, terminology, illustrations and/or arrangements set forth in the description or shown in the drawings. Rather, the invention is capable of embodiments in addition to those described and of being practiced and carried out in various ways and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

Aspects of the invention will be better understood from the following detailed description of the exemplary embodiments of the invention with reference to the drawings, in which FIG. 1 exemplarily shows a flow chart for a study design guide method 100.

DETAILED DESCRIPTION

Figure 1:
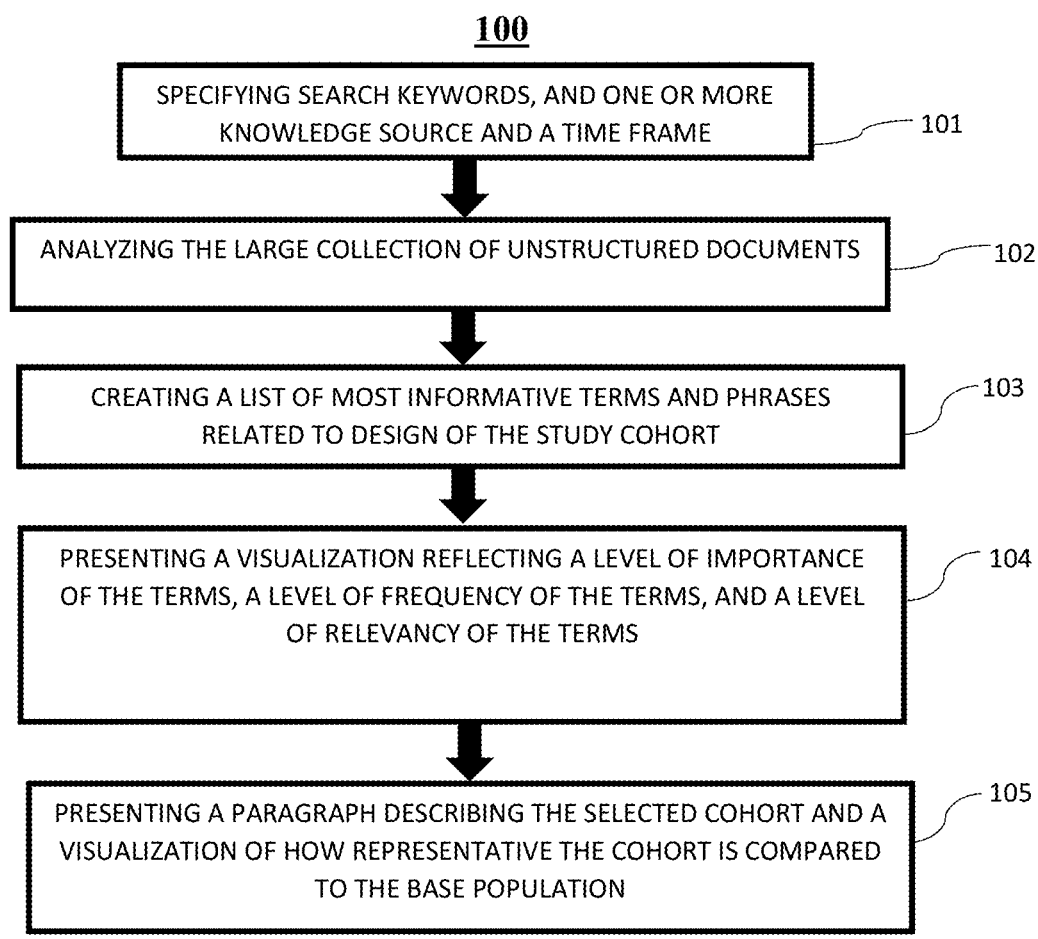

The invention will now be described with reference to FIGS. 1-8, in which like reference numerals refer to like parts throughout. It is emphasized that, according to common practice, the various features of the drawing are not necessarily to scale. On the contrary; the dimensions of the various features can be arbitrarily expanded or reduced for clarity With reference now to the example depicted in FIG. 1, the study design guide method 100 includes various steps using natural language processing (NLP) technology to quickly analyze a large amount of unstructured data and gets insights for cohort selection criteria and study design. As shown in at least FIG. 6, one or more computers of a computer system 12 according to an embodiment of the present invention can include a memory 28 having instructions stored in a storage system to perform the steps of FIG. 1.

Moreover, the method 100 can provide data quality information and comparison between selected vs. discarded subpopulations to inform the researcher on the effect of each selection step.

Thus, the study design guide method 100 according to an embodiment of the present invention may act in a more sophisticated, useful and cognitive manner, giving the impression of cognitive mental abilities and processes related to knowledge, attention, memory, judgment and evaluation, reasoning, and advanced computation. A system can be said to be "cognitive" if it possesses macro-scale properties—perception, goal-oriented behavior, learning/memory and action—that characterize systems (i.e., humans) generally recognized as cognitive.

Although one or more embodiments (see e.g., FIGS. 6-8) may be implemented in a cloud environment 50 (see e.g., FIG. 7), it is nonetheless understood that the present invention can be implemented outside of the cloud environment.

With reference generally to FIGS. 1-5, a user may specify search keywords including broad topics of interest, one or more of a disease, drug, test, procedure, or a combination of these, study design attributes data source, etc.

The user further specifies one or more knowledge sources (e.g. PubMed®, Google Scholar®, Clinicaltrials.gov, social media, etc.) and a time frame. This step restricts the search domain and may be important to the specific study parameters or domain. For example, medical literature has breakthroughs where a literature before a certain date may not have any value. Or, new standards are published that require an update on a cohort. A natural language processor (NLP) then analyzes the large collection of unstructured documents (e.g. methods sections of journal articles, conclusion sections, etc.) and creates a list of most informative terms/phrases related to design of the study cohort. In this way, a user can customize their study design.

Figure 2:
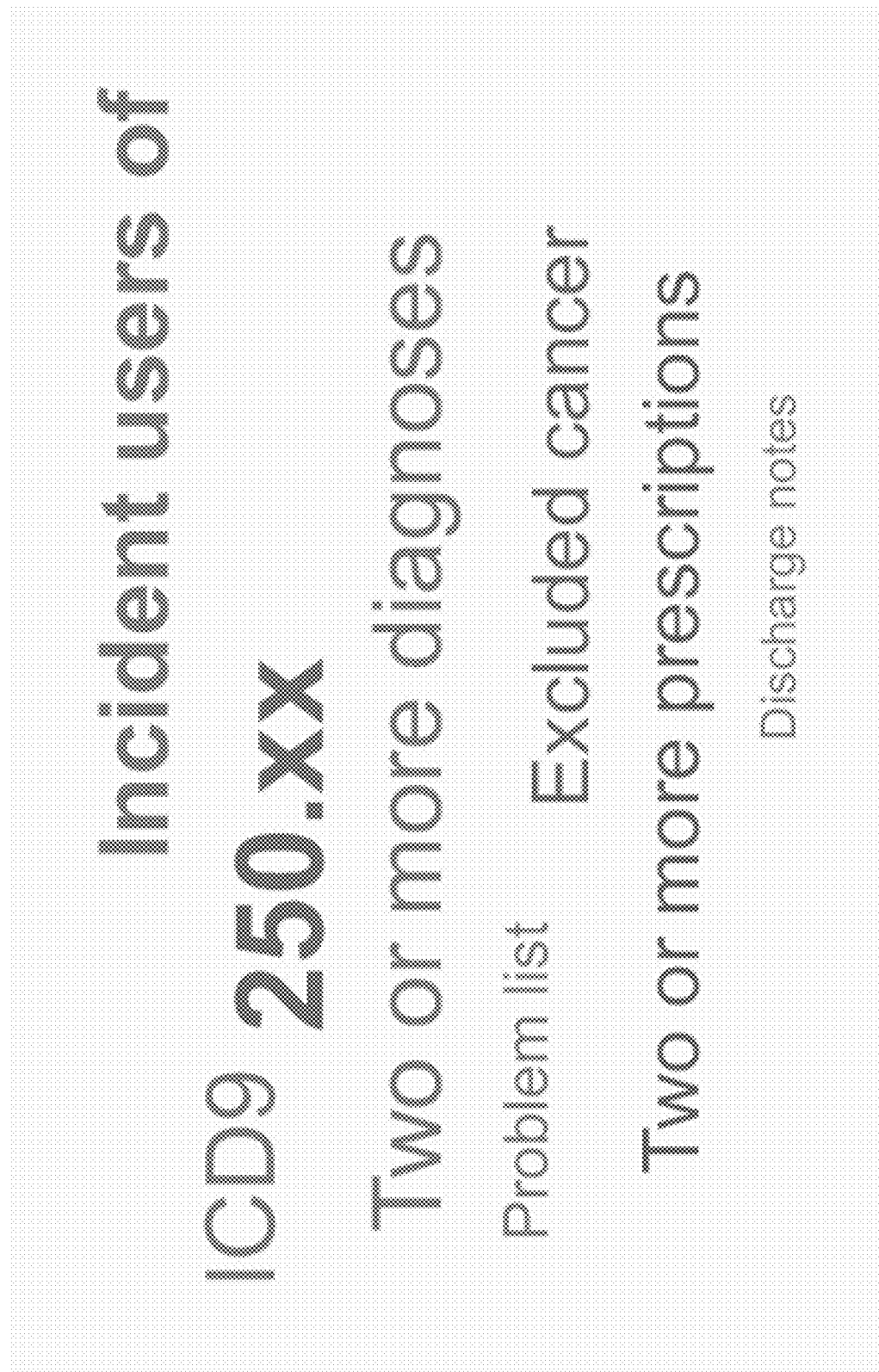
FIG. 2 exemplarily depicts a visualization reflecting a level of importance, a frequency, and a relevancy of the informative terms and the informative phrases according to an embodiment of the present invention.
Figure 3:
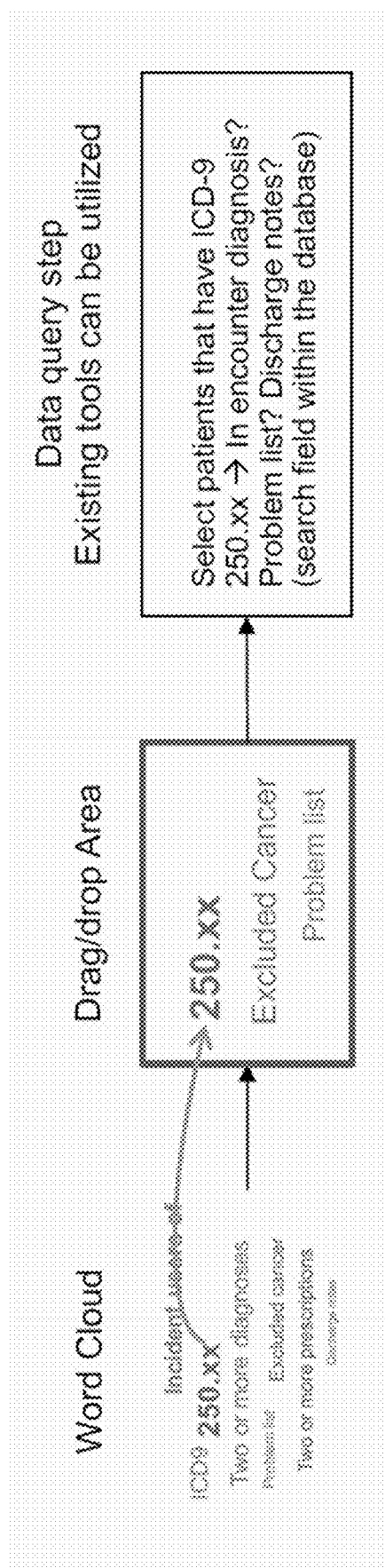
FIG. 3 exemplarily shows user-selected features applied to the user's study database according to an embodiment of the present invention.

The terms are then presented with visualization reflecting their level of importance, frequency, and relevancy (e.g. a "word cloud" with varying text size as exemplarily depicted in FIG. 2). As shown in FIG. 3, the user can select or drag/drop one or more of the terms on the interface to view analytics using his/her study data (e.g. prevalence of patients with the selected diagnosis) along with the quality of the data (e.g. percentage missing or variance of the selected variable).

A user can constrain the search output to pass through a medical language library (e.g. ICD, CPT/HCPCS, UMLS, etc.) to sieve out the non-medical terms. If multiple criteria are considered, then a visualization can be presented in a form of a Venn diagram. It can also provide the relationship between the selected terms.

Figure 4:
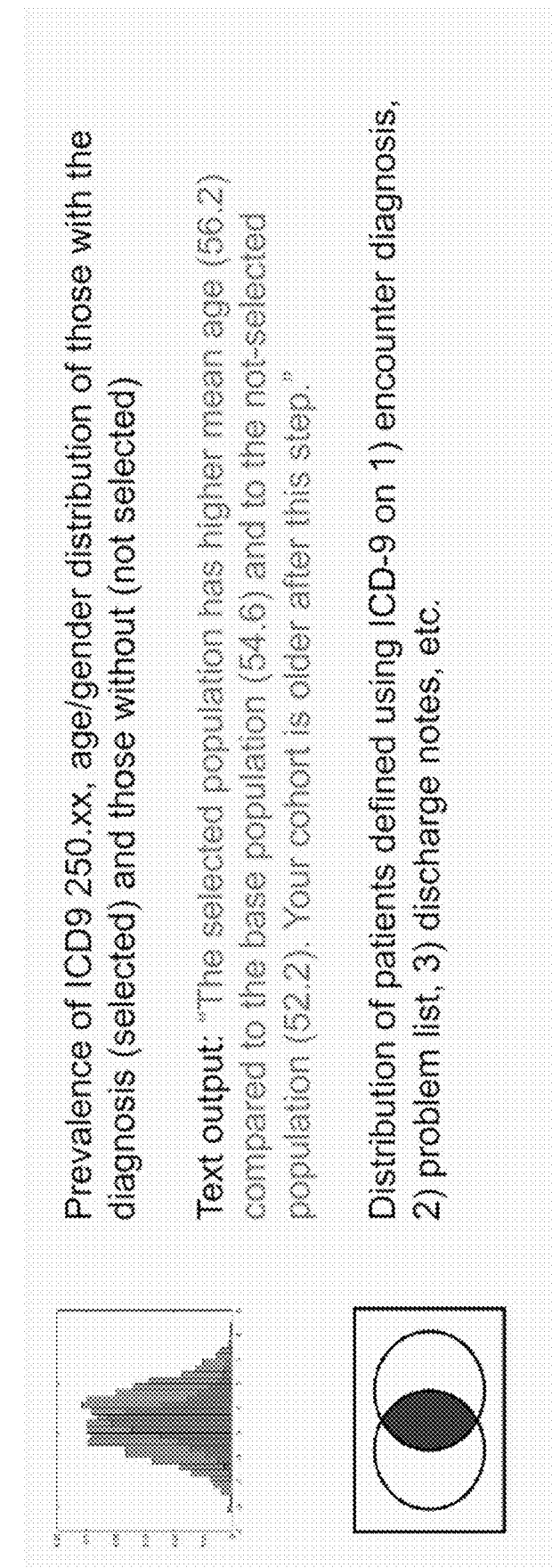
FIG. 4 exemplarily depicts a second visualization of descriptive analytics of the study cohort and the design cohort according to an embodiment of the invention.

After each selection, visualization of selected vs. discarded subpopulation characteristics are provided to help the user to recognize the effect of the selection (e.g., as shown in FIG. 4). Therefore, a user can compare their selection with a change in the cohort in real-time.

Figure 5:
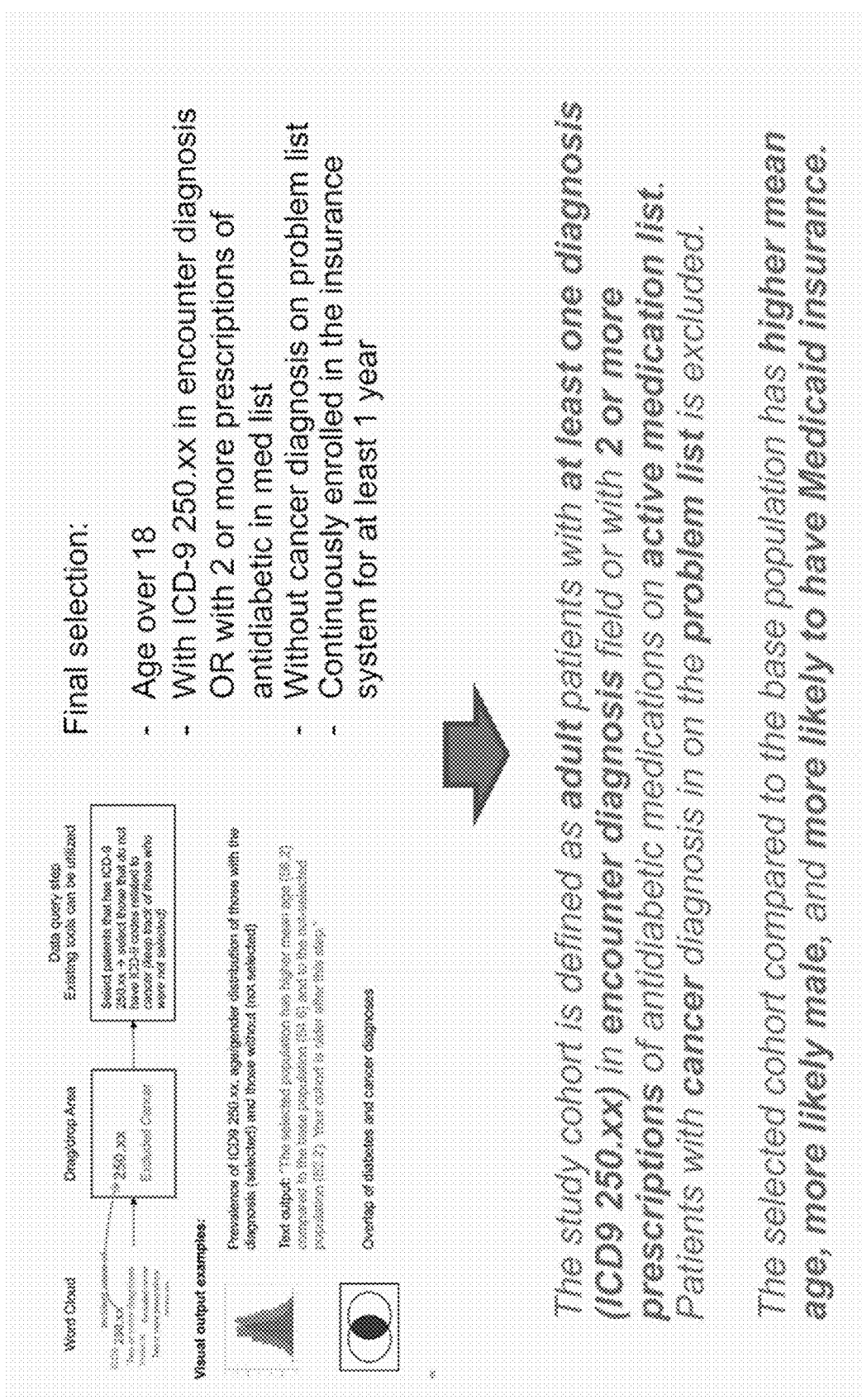
FIG. 5 exemplarily depicts a paragraph description of the study cohort and the design cohort according to an embodiment of the invention.

At the final step, the tool will present a paragraph (e.g., as depicted in FIG. 5) describing the selected cohort and a visualization of how representative the cohort is compared to the base population. The user will read and decide if the description matches his/her intention for the study.

With reference to FIG. 1, method 100 utilizes unstructured literature or web data to guide study design in healthcare databases. More specifically, in step 101, search parameters are specified including search keywords and one or more knowledge sources and a time frame.

In step 102, the large collection of unstructured documents are analyzed (e.g. methods sections of journal articles). In step 103, a list of most informative terms/phrases related to design of the study cohort are created. In step 104, a user is presented with visualization reflecting their level of importance/frequency/relevancy. And, in step 105, a user is presented a paragraph describing the selected cohort and a visualization of how representative the cohort is compared to the base population.

FIGS. 2-5 exemplarily depict a use case illustrating the benefits of the instant invention. For example, a study question of "Is drug A more effective than drug HbA1c control in adult type 2 diabetic patients?" can be explored by the invention.

Based on the question, a user can input search keywords as

"User input 1|search keywords:

Topic of interest: "diabetes", "Type 2 diabetes", "drug A", "drug B", "A1c";

Study design: "comparative effectiveness", "cohort study";

Cohort attributes: "adult", "US"; and

Data source: "EMR data", "Clinical trials data", "questionnaire data", "claims data", "administrative data"".

And, the user can indicate the knowledge source and a time frame as

"User input 2:

Knowledge source: "PubMed", "Google Scholar", "Web of Science", "Clinicaltials.gov"; and Time frame: published between "2000" and "2017"".

Based on the user inputs 1 and 2, the NLP reads through a large number of clinical literature about diabetes treatment with user-input features, focuses on "Methods" section of journal abstracts and articles, trial protocols, etc., and uses natural language processing to find terms/phrases that were used to define study cohort. The tool may combine multiple terms/phrases if they have the same meaning.

Cohort characteristics in phrase/words are extracted. For example, the invention can extract the following exemplary phrases/words:

Based on 'diagnostic codes': "ICD-9 code 250.0x", "two or more codes of", "diagnosis on problem list", "discharge notes";

Based on 'treatments': "had a prescription of [medication]", "two or more prescriptions";

(combined "two prescriptions", "two or more prescriptions", and other similar phrases), "on active medication list"; and Other criteria: "A1c above 7" (combined "A1c>7", "HbA1c 7 or above", and other similar phrases), "excluded patients with [diagnosis]", "incident users of [medication]", "no prescription during the prior 6 months".

The extracted phrases/words are visualized in a word/phrase cloud based on the frequency as depicted in FIG. 2. Related/similar concepts may be combined into one phrase such as "ICD-9 250.xx" and "diabetes diagnostic code" may be combined into "ICD-9 codes 250.xx".

Then, user-selected features will be applied to the user's study database and descriptive analytics will be provided. For example, as exemplarily depicted in FIG. 3, a user can drag and drop words or phrases using a graphical user interface (GUI) into a drag/drop area from the word cloud (e.g., step 103 and 104). Based on the selected terms, a data query step can be performed.

FIG. 4 exemplarily depicts an output of step 104 of visual output examples such as a chart, a graph, or a description. For example, based on the selected "prevalence of ICD9 250.xx, age/gender distribution of those with the diagnosis (selected) and those without (not selected)", a text output can be shown of "The selected population has higher mean age (56.2) compared to the base population (54.6) and to the not-selected population (52.2). Your cohort is older after this step." and a distribution of patients defined using ICD-9 on 1) encounter diagnosis, 2) problem list, 3) discharge notes, etc. can be visualized.

That is, FIG. 4 depicts a change in the cohort based on a user selection of different terms and phrases for building their cohort. The user can visualize, in real-time, the effects on their design study from changing their cohort. And, a text output indicating the changes can be output such as "The selected population has higher mean age (56.2) compared to the base population (54.6) and to the not-selected population (52.2). Your cohort is older after this step."

And, as depicted in FIG. 5, a description of the cohort in natural language can be provided for cognitive support for the user in determining the study design and study cohort. That is, based on a final selection, the paragraph can be presented to assist the user (e.g., step 105). Also, the paragraph can explain the cohort to the user for their design study.

Thereby, clinical researchers can identify target population for research purposes, with reduced time spent on a background search. The invention can improve the quality of clinical studies and publications by providing evidence for and explicit description of the design rationale. Moreover, the invention can be used to build disease registry for or drug registry easily with existing data that is clinically meaningful and generalizable.

Exemplary Aspects, Using a Cloud Computing Environment

Although this detailed description includes an exemplary embodiment of the present invention in a cloud computing environment, it is to be understood that implementation of the teachings recited herein are not limited to such a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client circuits through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
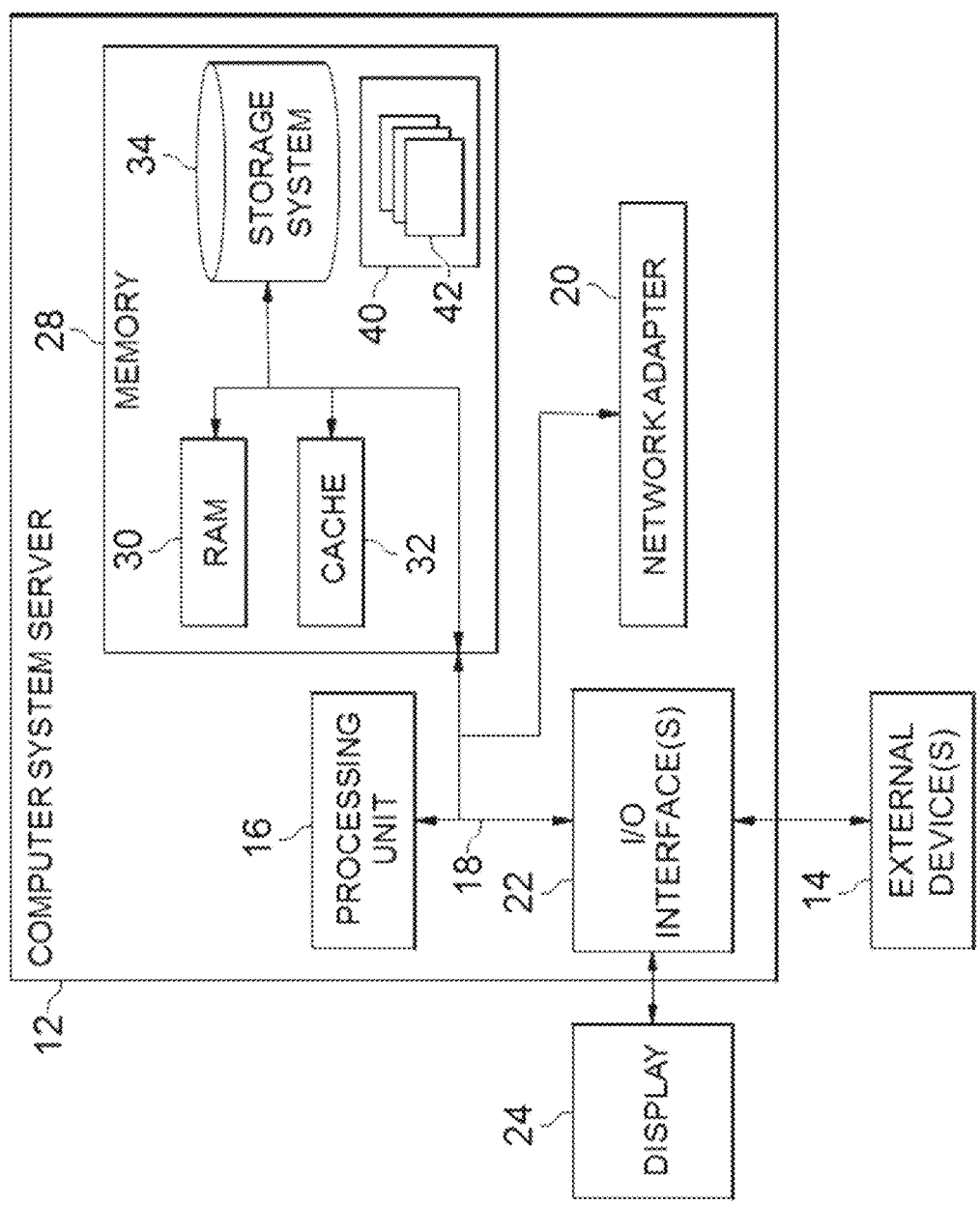
FIG. 6 depicts a cloud computing node 10 according to an embodiment of the present invention.

Referring now to FIG. 6, a schematic of an example of a cloud computing node is shown. Cloud computing node 10 is only one example of a suitable node and is not intended to suggest any limitation as to the scope of use or functionality of embodiments of the invention described herein. Regardless, cloud computing node 10 is capable of being implemented and/or performing any of the functionality set forth herein.

Although cloud computing node 10 is depicted as a computer system/server 12, it is understood to be operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop circuits, multiprocessor systems, microprocessor-based systems, set top boxes, programmable consumer electronics, network PCs, minicomputer systems, mainframe computer systems, and distributed cloud computing environments that include any of the above systems or circuits, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing circuits that are linked through a communications network. In a distributed cloud computing environment, program modules may be located in both local and remote computer system storage media including memory storage circuits.

Referring again to FIG. 6, computer system/server 12 is shown in the form of a general-purpose computing circuit. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to early out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external circuits 14 such as a keyboard, a pointing circuit, a display 24, etc.; one or more circuits that enable a user to interact with computer system/server 12; and/or any circuits (e.g., network card, modem, etc.) that enable computer system/server 12 to communicate with one or more other computing circuits. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, circuit drivers, redundant processing units, external disk drive arrays, RAID systems, tape drives, and data archival storage systems, etc.

Figure 7:
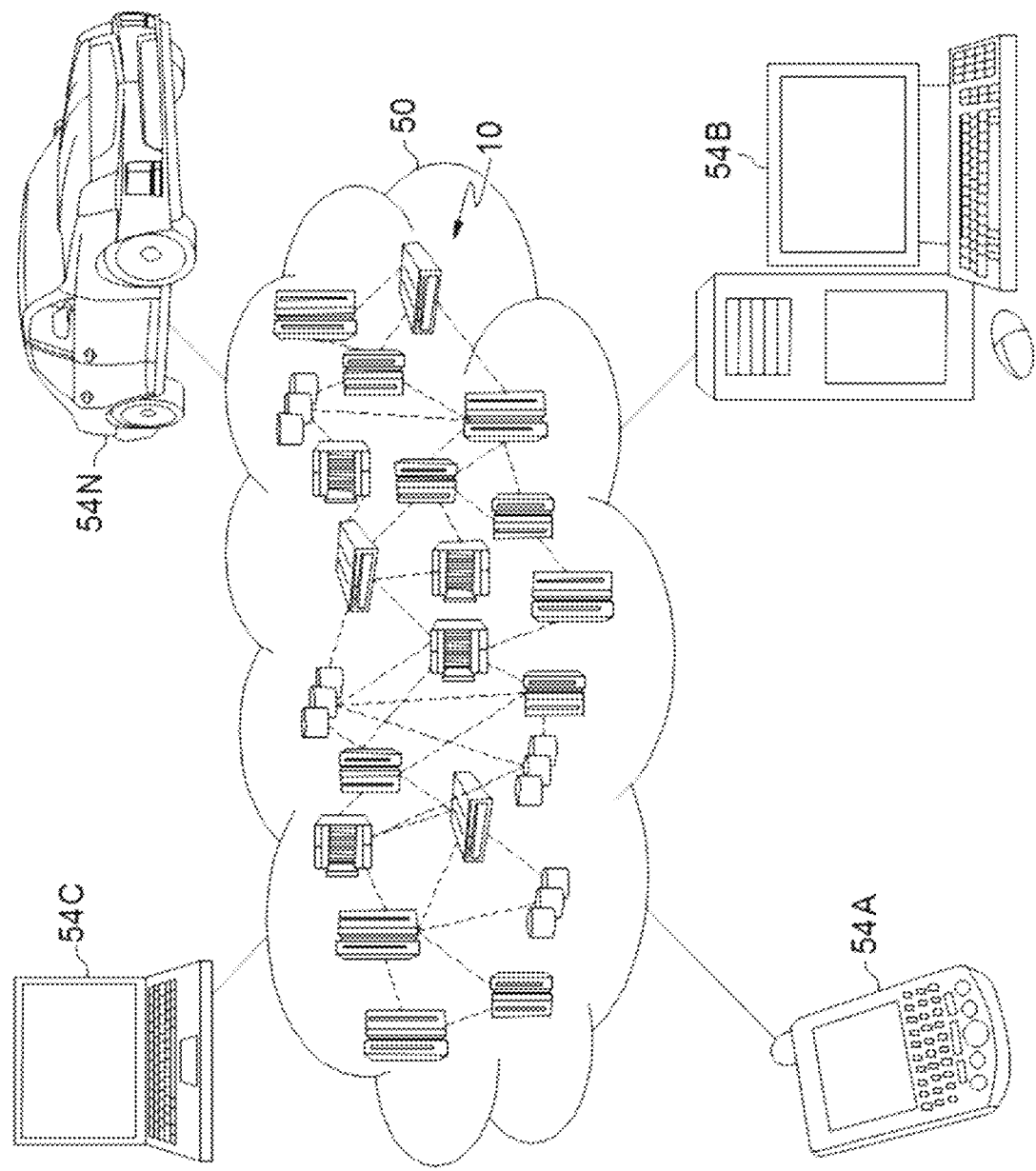
FIG. 7 depicts a cloud computing environment 50 according to an embodiment of the present invention.

Referring now to FIG. 7, illustrative cloud computing environment 50 is depicted. As shown, cloud computing environment 50 comprises one or more cloud computing nodes 10 with which local computing circuits used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped. (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing circuit. It is understood that the types of computing circuits 54A-N shown in FIG. 7 are intended to be illustrative only and that computing nodes 10 and cloud computing environment 50 can communicate with any type of computerized circuit over any type of network and/or network addressable connection. (e.g., using a web browser).

Figure 8:
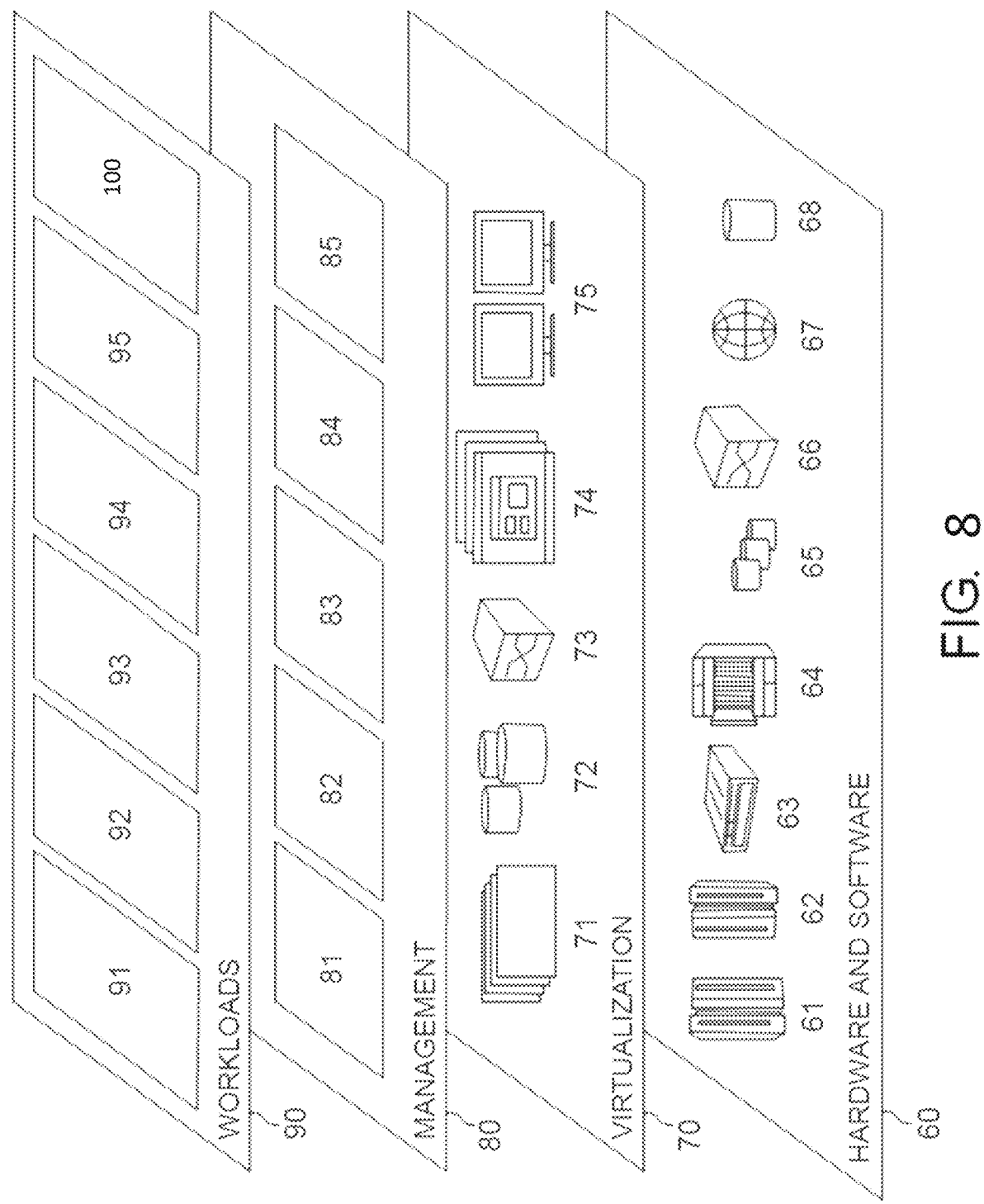
FIG. 8 depicts abstraction model layers according to an embodiment of the present invention.

Referring now to FIG. 8, an exemplary set of functional abstraction layers provided by cloud computing environment 50 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage circuits 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom cation delivery 93; data analytics processing 94; transaction processing 95; and, more particularly relative to the present invention, the study design guide method 100.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function; act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further, Applicant's intent is to encompass the equivalents of all claim elements, and no amendment to any claim of the present application should be construed as a disclaimer of any interest in or right to an equivalent of any element or feature of the amended claim.

What is claimed is:

1. A computer-implemented study design guide method, the method comprising:
    specifying a search parameter including a time frame;
    analyzing, via a natural language processor operating at a cloud computing node, a collection of unstructured documents using the search parameter by restricting the collection of the unstructured documents to a publication date within the time frame to create a narrowed version of the collection of the unstructured documents;
    creating a list of informative terms and informative phrases related to design of a study cohort based on the analysis of the narrowed version of the collection of unstructured documents and within the time frame;
    creating a graphical visualization of the list of informative terms and informative phrases by varying a graphical display of each of the information terms and informative phrases to emphasize a level of importance, frequency, and relevancy, via an interactive Graphical User Interface (GUI) that is provided at a client server node on a client device;
    forming the study cohort by selecting a subset from the narrowed version of the unstructured documents by filtering the narrowed version of the unstructured documents using-a drag/drop feature and a drag/drop area on the client device for selecting an informative term and an informative phrase from the list of informative terms and informative phrases by dragging a selection into the drag/drop area;
    providing a paragraph description having a complete sentence describing the study cohort that is selected according to the informative term and the informative phrase in the drag/drop area; and
    creating, via the cloud computing node, a second graphical visualization reflecting the level of importance, the frequency, and the relevancy of the informative terms and the informative phrases in relation to each other for a study design using the study cohort,
    wherein, after the selecting the subset, a third graphical visualization of the selected subset versus a discarded subpopulation characteristics is provided to the client server node from the cloud computing node to visually compare the selection.

2. The computer-implemented method of claim 1, further comprising presenting a visual description that describes the study cohort of how representative the study cohort is compared to a base population.

3. The computer-implemented method of claim 1, further comprising presenting a visual description and a paragraph describing the study cohort of how representative the study cohort is compared to a base population.

4. The computer-implemented method of claim 1, wherein the search parameter is selected from a group consisting of:
    a search keyword; and
    a knowledge source.

5. The computer-implemented method of claim 1, wherein the collection of unstructured documents comprises health care documents.

6. The computer-implemented method of claim 1, embodied in a cloud-computing environment.

7. A computer program product, the computer program product comprising a computer-readable storage medium having program instructions embodied therewith, the program instructions executable by a computer to cause the computer to perform:
    specifying a search parameter including a time frame;
    analyzing, via a natural language processor operating at a cloud computing node, a collection of unstructured documents using the search parameter by restricting the collection of the unstructured documents to a publication date within the time frame to create a narrowed version of the collection of the unstructured documents;
    creating a list of informative terms and informative phrases related to design of a study cohort based on the analysis of the narrowed version of the collection of unstructured documents and within the time frame;
    creating a graphical visualization of the list of informative terms and informative phrases by varying a graphical display of each of the information terms and informative phrases to emphasize a level of importance, frequency, and relevancy, via an interactive Graphical User Interface (GUI) that is provided at a client server node on a client device;
    forming the study cohort by selecting a subset from the narrowed version of the unstructured documents by filtering the narrowed version of the unstructured documents using a drag/drop feature and a drag/drop area on the client device for selecting an informative term and an informative phrase from the list of informative terms and informative phrases by dragging a selection into the drag/drop area;
    providing a paragraph description having a complete sentence describing the study cohort that is selected according to the informative term and the informative phrase in the drag/drop area; and
    creating, via the cloud computing node, a second graphical visualization reflecting the level of importance, the frequency, and the relevancy of the informative terms and the informative phrases in relation to each other for a study design using the study cohort, wherein, after the selecting the subset, a third graphical visualization of the selected subset versus a discarded subpopulation characteristics is provided to the client server node from the cloud computing node to visually compare the selection.

8. The computer program product of claim 7, further comprising presenting a visual description that describes the study cohort of how representative the study cohort is compared to a base population.

9. The computer program product of claim 7, further comprising presenting a visual description and a paragraph describing the study cohort of how representative the study cohort is compared to a base population.

10. The computer program product of claim 7, wherein the search parameter is selected from a group consisting of:
a search keyword; and
a knowledge source.

11. The computer program product of claim 7, wherein the collection of unstructured documents comprises health care documents.

12. A computer-implemented study design guide system, said system comprising:
a processor; and
a memory, the memory storing instructions to cause the processor to perform:
specifying a search parameter including a time frame;
analyzing, via a natural language processor operating at a cloud computing node, a collection of unstructured documents using the search parameter by restricting the collection of the unstructured documents to a publication date within the time frame to create a narrowed version of the collection of the unstructured documents;
creating a list of informative terms and informative phrases related to design of a study cohort based on the analysis of the narrowed version of the collection of unstructured documents and within the time frame;
creating a graphical visualization of the list of informative terms and informative phrases by varying a graphical display of each of the information terms and informative phrases to emphasize a level of importance, frequency, and relevancy, via an interactive Graphical User Interface (GUI) that is provided at a client server node on a client device;
forming the study cohort by selecting a subset from the narrowed version of the unstructured documents by filtering the narrowed version of the unstructured documents using a drag/drop feature and a drag/drop area on the client device for selecting an informative term and an informative phrase from the list of informative terms and informative phrases by dragging a selection into the drag/drop area;
providing a paragraph description having a complete sentence describing the study cohort that is selected according to the informative term and the informative phrase in the drag/drop area; and
creating, via the cloud computing node, a second graphical visualization reflecting the level of importance, the frequency, and the relevancy of the informative terms and the informative phrases in relation to each other for a study design using the study cohort,
wherein, after the selecting the subset, a third graphical visualization of the selected subset versus a discarded subpopulation characteristics is provided to the client server node from the cloud computing node to visually compare the selection.

13. The system of claim 12, embodied in a cloud-computing environment.

* * * * *